United States Patent
Osmundsen et al.

(10) Patent No.: US 11,384,038 B2
(45) Date of Patent: *Jul. 12, 2022

(54) PROCESS FOR THE PREPARATION OF ETHYLENE GLYCOL FROM SUGARS

(71) Applicant: HALDOR TOPSØE A/S, Kgs. Lyngby (DK)

(72) Inventors: Christian Mårup Osmundsen, Gentofte (DK); Esben Taarning, Frederiksberg (DK); Morten Boberg Larsen, Smørum (DK)

(73) Assignee: HALDOR TOPSØE A/S, Kgs. Lyngby (DK)

(*) Notice: Subject to any disclaimer, the term of this patent is extended or adjusted under 35 U.S.C. 154(b) by 0 days.

This patent is subject to a terminal disclaimer.

(21) Appl. No.: 16/068,472

(22) PCT Filed: Jan. 5, 2017

(86) PCT No.: PCT/EP2017/050215
§ 371 (c)(1),
(2) Date: Jul. 6, 2018

(87) PCT Pub. No.: WO2017/118701
PCT Pub. Date: Jul. 13, 2017

(65) Prior Publication Data
US 2019/0010103 A1 Jan. 10, 2019

(30) Foreign Application Priority Data
Jan. 7, 2016 (DK) .......................... PA 2016 00006

(51) Int. Cl.
| | | |
|---|---|---|
| *C07C 29/141* | (2006.01) | |
| *C07C 27/00* | (2006.01) | |
| *B01J 21/18* | (2006.01) | |
| *B01J 23/72* | (2006.01) | |
| *C07C 27/04* | (2006.01) | |
| *C07C 31/20* | (2006.01) | |
| *B01J 19/24* | (2006.01) | |

(52) U.S. Cl.
CPC ............. *C07C 29/141* (2013.01); *B01J 21/18* (2013.01); *B01J 23/72* (2013.01); *C07C 27/00* (2013.01); *C07C 27/04* (2013.01); *C07C 31/202* (2013.01); *B01J 19/24* (2013.01); *Y02P 20/129* (2015.11); *Y02P 20/52* (2015.11)

(58) Field of Classification Search
CPC .. B01J 19/24; B01J 21/18; B01J 23/72; C07C 29/141; C07C 31/202; C07C 27/00; C07C 27/04; Y02P 20/132; Y02P 20/52
See application file for complete search history.

(56) References Cited

U.S. PATENT DOCUMENTS

| | | | |
|---|---|---|---|
| 4,094,914 A * | 6/1978 | Rottig | ................... C07C 29/141 |
| | | | 568/862 |
| 4,200,765 A | 4/1980 | Goetz | |
| 4,317,946 A | 3/1982 | Costa | |
| 4,321,414 A | 3/1982 | Costa | |
| 4,405,821 A * | 9/1983 | Goetz | .................... C07C 29/38 |
| | | | 568/462 |
| 4,496,781 A | 1/1985 | Jacobson et al. | |
| 4,762,817 A | 8/1988 | Logsdon et al. | |
| 5,210,337 A | 5/1993 | Broussard | |
| 5,334,778 A | 8/1994 | Hass et al. | |
| 5,393,542 A | 2/1995 | Stradal et al. | |
| 6,096,931 A | 8/2000 | Frohning et al. | |
| 6,255,541 B1 | 7/2001 | Paatero et al. | |
| 6,297,408 B1 | 10/2001 | Hass et al. | |
| 6,297,409 B1 | 10/2001 | Choque et al. | |
| 6,486,366 B1 * | 11/2002 | Ostgard | ................ C07C 29/141 |
| | | | 568/862 |
| 7,094,932 B2 | 8/2006 | Majerski et al. | |
| 9,126,912 B1 | 9/2015 | Chen et al. | |
| 9,926,247 B2 * | 3/2018 | Marup | .................... C07C 27/00 |
| 10,077,222 B2 * | 9/2018 | Holm | .................... C07C 29/141 |
| 2004/0022912 A1 | 2/2004 | Majerski et al. | |
| 2005/0244312 A1 | 11/2005 | Suppes et al. | |
| 2007/0249871 A1 | 10/2007 | Almeida Lenero et al. | |
| 2007/0287868 A1 | 12/2007 | Arredondo et al. | |
| 2008/0045749 A1 | 2/2008 | Arredondo et al. | |
| 2008/0228014 A1 | 9/2008 | Bloom | |
| 2011/0021845 A1 | 1/2011 | Zim et al. | |
| 2012/0172633 A1 | 7/2012 | Zhang et al. | |

(Continued)

FOREIGN PATENT DOCUMENTS

| | | |
|---|---|---|
| CN | 1221723 A | 7/1999 |
| CN | 1894188 A | 1/2007 |

(Continued)

OTHER PUBLICATIONS

Serban C. Moldoveanu ("Pyrolysis of Aldehydes and Ketones", Pyrolysis of Organic Molecules (Second Edition), 2019, pp. 391-418).*
Diatomite, International Cenological Codex, Oct. 2002, pp. 1-3 (Year: 2002).*
Indo German Carbons Limited, "Activated Carbon", https:www.igcl.com/php/activated_carbon.php, 2006, pp. 1-3. (Year: 2006).*
Office Action issued by the U.S. Patent and Trademark Office in the U.S. Appl. No. 16/068,581, dated Mar. 28, 2019, U.S. Patent and Trademark Office, Alexandria, VA. (14 pages).
Office Action dated May 9, 2019, by the Taiwanese Patent Office in corresponding Taiwanese Patent Application No. 104121105, and an English Translation of the Office Action. (14 pages).

(Continued)

*Primary Examiner* — Rosalynd A Keys
(74) *Attorney, Agent, or Firm* — Buchanan Ingersoll & Rooney P.C.

(57) ABSTRACT

A process for the preparation of ethylene glycol and other $C_1$-$C_3$ hydroxy compounds comprising the steps of hydrogenating a composition comprising $C_1$-$C_3$ oxygenate compounds in the gas phase in the presence of a copper on carbon catalyst.

23 Claims, 2 Drawing Sheets

(56) References Cited

U.S. PATENT DOCUMENTS

| | | |
|---|---|---|
| 2013/0253230 A1 | 9/2013 | Norman et al. |
| 2013/0338405 A1 | 12/2013 | Kizaki et al. |
| 2014/0039224 A1 | 2/2014 | Adlaf et al. |
| 2015/0329449 A1 | 11/2015 | Schreck et al. |
| 2016/0177185 A1 | 6/2016 | Bauer et al. |
| 2017/0009008 A1 | 1/2017 | Van Walsem et al. |
| 2017/0197893 A1 | 7/2017 | Marup et al. |

FOREIGN PATENT DOCUMENTS

| | | |
|---|---|---|
| CN | 101925569 A | 12/2010 |
| CN | 102190562 A | 9/2011 |
| CN | 102649081 A | 8/2012 |
| CN | 102781897 A | 11/2012 |
| CN | 106470965 A | 3/2017 |
| EP | 0 002 908 B1 | 5/1982 |
| EP | 0 922 687 A | 6/1999 |
| JP | S5118928 B1 | 6/1976 |
| JP | S60218341 A | 11/1985 |
| JP | 2013520486 A | 6/2013 |
| JP | 2017519793 A | 7/2017 |
| RU | 2351581 C2 | 4/2009 |
| TW | 470739 B | 1/2002 |
| TW | 201229015 A1 | 7/2012 |
| WO | 00/14041 A1 | 3/2000 |
| WO | 2005/037749 A1 | 4/2005 |
| WO | 2005/058788 A1 | 6/2005 |
| WO | 2011/138643 A2 | 11/2011 |
| WO | 2012096323 A1 | 7/2012 |
| WO | 2015/055315 A1 | 4/2015 |
| WO | 2015154258 A1 | 10/2015 |
| WO | 2016/001136 A1 | 1/2016 |

OTHER PUBLICATIONS

Hawley's Condensed Chemical Dictionary (recycling, Mar. 2007, 1 page).

International Search Report (PCT/ISA/210) dated Mar. 29, 2017, by the European Patent Office as the International Searching Authority for International Application No. PCT/EP2017/050183.

Written Opinion (PCT/ISA/237) dated Mar. 29, 2017, by the European Patent Office as the International Searching Authority for International Application No. PCT/EP2017/050183.

Danish Search Report of Danish Patent Application No. PA 2016 00006, dated Jul. 26, 2016.

International Search Report (PCT/ISA/210) dated Mar. 24, 2017, by the European Patent Office as the International Searching Authority for International Application No. PCT/EP2017/050215.

Written Opinion (PCT/ISA/237) dated Mar. 25, 2017, by the European Patent Office as the International Searching Authority for International Application No. PCT/EP2017/050215.

Office Action dated Mar. 26, 2020, by the Federal Service for Intellectual Property in Russian Patent Application No. 2018128531/04(045794). (18 pages).

Office Action (The First Office Action) dated Aug. 24, 2020 by the China National Intellectual Property Administration in corresponding Chinese Patent Application No. 201780005774.5, and an English Translation of the Office Action. (17 pages).

Office Action dated Oct. 9, 2020, by the Japanese Patent Office in corresponding Japanese Patent Application No. 2018-535302, and an English Translation of the Office Action. (10 pages).

Office Action dated Apr. 23, 2021, by the Taiwan Intellectual Property Office in corresponding Taiwanese Patent Application No. 106100430, and an English Translation of the Office Action. (26 pages).

\* cited by examiner

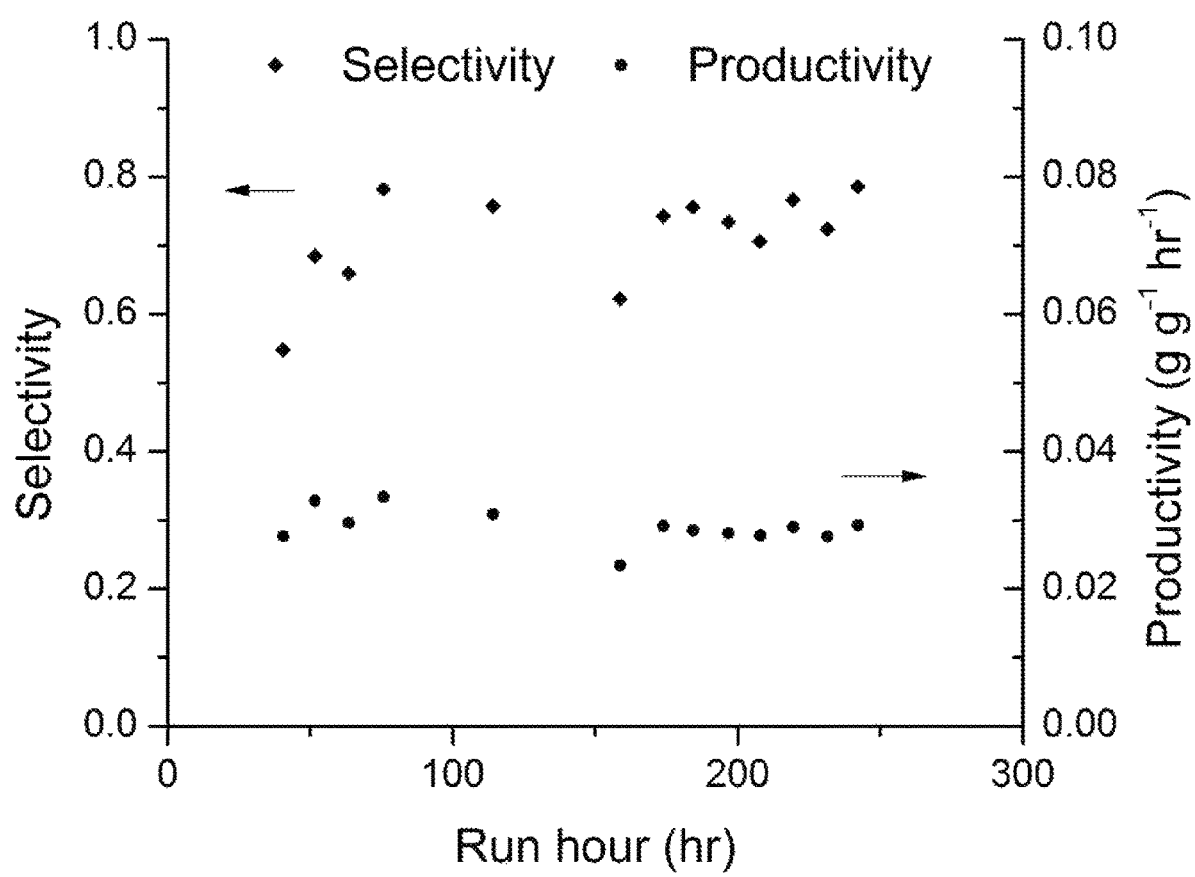

PROCESS FOR THE PREPARATION OF ETHYLENE GLYCOL FROM SUGARS

TECHNICAL FIELD

The invention regards an improved hydrogenation process for catalytic hydrogenation of low molecular weight oxygenate compounds to its hydroxyl counterparts. In particular, the conversion is a gas phase conversion using a catalyst based on copper on carbon. The method is suitable for converting a $C_1$-$C_3$ oxygenate composition obtained from thermolytic fragmentation of a sugar composition.

BACKGROUND

Ethylene glycol can be prepared by a variety of routes including from sugars, e.g. monosaccharides, disaccharides or syrups, via fermentation and hydrogenolysis processes, or by hydroformylation of formaldehyde.

The fermentation route is a five-step process wherein glucose is fermented to ethanol and carbon dioxide, followed by conversion of ethanol to ethylene, ethylene to ethylene oxide and ethylene oxide to ethylene glycol. One disadvantage of this method is that per mole of glucose fermented, two moles of carbon dioxide are produced together with two moles of ethanol; this has the effect that a theoretical maximum 67% of the carbon present in the glucose can be transformed to ethanol.

The hydrogenolysis route is a two-step process wherein glucose is reduced to sorbitol followed by hydrogenolysis of sorbitol to ethylene glycol, as illustrated by U.S. Pat. No. 6,297,409 B1 and US 2008/0228014 A1. Significant quantities of propylene glycol, compared to ethylene glycol, are formed via the hydrogenolysis process. Additionally, the amount of catalyst used is significant and appears difficult to regenerate in order to reuse. Furthermore, the byproducts formed, in particular butanediols, are difficult to separate from the desired product. In particular, the industrially favorable method of distillation for separation (purification) purposes is extremely difficult to apply as the byproducts have very similar boiling points to the final product, and the desired product may react further, as illustrated in US2014/0039224 A1 and U.S. Pat. No. 5,393,542 B1.

The hydroformylation route is a two-step process wherein glycolaldehyde is prepared from formaldehyde, carbon monoxide and hydrogen, followed by hydrogenation of the glycolaldehyde to ethylene glycol, as illustrated in U.S. Pat. No. 4,496,781 B1. There appears to be several extraction steps present in order to separate formaldehyde from glycolaldehyde and proceed with the hydrogenation reaction.

It is known that sugars may be subjected to thermolytic fragmentation to obtain a fragmentation product composition comprising oxygenate compounds such as glycolaldehyde (U.S. Pat. No. 7,094,932 B2); the crude fragmentation product composition comprises $C_1$-$C_3$ oxygenate compounds, including formaldehyde, glycolaldehyde, glyoxal, pyruvaldehyde and acetol. It is thus a complex composition of products having different physicochemical properties. The main product of this reaction is glycolaldehyde [U.S. Pat. No. 7,094,932 B2]. Water is the solvent of the reaction.

It is also known that pure glycolaldehyde may be hydrogenated to ethylene glycol. U.S. Pat. No. 4,200,765 B1 discloses hydrogenation of glycolaldehyde under severe conditions: at high pressure [3000 psi (ca. 202 bar)], high temperature [150° C.], and with an organic solvent [N-methyl pyrrolidine] in the presence of a palladium on carbon [Pd/C] catalyst for an extended period [5 h]. U.S. Pat. No. 4,321,414 B1 and U.S. Pat. No. 4,317,946 B1 disclose the hydrogenation of glycolaldehyde with a homogenous ruthenium catalyst and U.S. Pat. No. 4,496,781 B1 discloses a continuous flow hydrogenation at low pressure [500 psi (ca. 35 bar)], high temperature [160° C.] with a ruthenium on carbon catalyst [Ru/C] in ethylene glycol and trace acetonitrile as solvent.

As illustrated, the two steps, thermolytic fragmentation of glucose to obtain, inter alia glycolaldehyde, and hydrogenation of pure glycolaldehyde in the liquid phase, appear to be independently feasible. However, in order for the fragmentation product composition to be hydrogenated, laborious separation processes are employed to remove formaldehyde from the fragmentation product composition to avoid formaldehyde poisoning of the hydrogenation catalysts [U.S. Pat. No. 5,210,337 B1]. U.S. Pat. No. 5,393,542 B1 discloses an exemplary purification process comprising multiple distillation steps followed by a solvent-induced precipitation to obtain a glycolaldehyde composition free of formaldehyde.

With regard to hydrogenation of glycolaldehyde, although there is the provision of suitable reaction conditions to obtain a high yield in organic solvents, the reaction with water as a solvent appears to be less successful. U.S. Pat. No. 5,393,542 B1 discloses thermal degradation of glycolaldehyde (2-hydroxyacetaldehyde) when subjected to temperatures of 90° C. or higher and where water is the solvent.

EP 0 002 908 B1 discloses the variation in yield (conversion and selectivity) of the hydrogenation of glycolaldehyde with the use of various catalysts in an aqueous solution at 110° C.: Raney Nickel [100% conversion 49.4% selectivity], 10% Pd/C [62% conversion, 61% selectivity] and 10% Pt/C [100% conversion, 73% selectivity]. A problem with catalysts used in liquid water is the strain on the catalyst. However, mild reaction conditions are favorable in order to ensure longevity of the catalyst on an industrial scale.

The choice of catalyst may affect the decomposition of glycolaldehyde when in the presence of the catalyst; U.S. Pat. No. 5,210,337 B1 discloses the problem of glycolaldehyde 'unzipping' to form formaldehyde and consequently poisoning the hydrogenation catalyst. It is also possible that glycolaldehyde may self-condense or condense with another $C_1$-$C_3$ oxygenate compound, also illustrated in U.S. Pat. No. 5,210,337 B1. Accordingly, both the choice of catalyst and the stability of the glycol product may affect the degree of reduction of the glycolaldehyde. E.g. some catalysts may reduce the glycolaldehyde to ethanol or ethane, i.e. over-reduce the glycolaldehyde.

Additionally, it is known that an increase in factors such as temperature, pressure, concentration of substrate and/or concentration of product as well as the amount and identity of catalyst present may affect the yield (conversion and selectivity) of hydrogenation reactions of glycolaldehyde. Handbook of Heterogeneous Catalytic Hydrogenation for Organic Synthesis, Shigeo Nishimura, ISBN: 978-0-471-39698-7, April 2001.

Indeed, the efforts to provide an industrial scale process for hydrogenation of the complex fragmentation product composition of an industrial scale thermolytic fragmentation of sugars to produce ethylene glycol have shown to be challenging. Formaldehyde formed in the thermolytic fragmentation has shown to poison the hydrogenation catalyst, even at low formaldehyde concentrations. The reaction conditions have shown to affect the selectivity, conversion rate and hydrogenation catalyst lifetime. Finally, formation of unwanted side products represents a loss of material and thus a loss of value and in addition the side-products may complicate the subsequent purification of the hydrogenation product composition.

Consequently, there is still a need for improving the processes of producing ethylene glycol from sugars via thermolytic fragmentation of sugars followed by catalytic hydrogenation of the resulting fragmentation product composition to avoid toxic compositions, obtain higher yields and higher selectivities and reduce the amount of undesirable side-products. In order to provide processes suitable for industrial scale production of ethylene glycol, such processes must be economically competitive.

SUMMARY OF INVENTION

In order to design an industrial scale production of ethylene glycol and other $C_1$-$C_3$ hydroxy compounds from biomaterials, such as sugar compositions, there is a desire to improve efficiency. In general, this includes increasing the load of substrates, reducing the amount and increasing the life time of catalyst materials and reducing the amount of side products.

The inventors have surprisingly found, that conducting the catalytic hydrogenation reaction in the gas phase in the presence of a catalyst material based on Cu on carbon provides a number of advantages.

Process of Producing $C_1$-$C_3$ Hydroxy Compounds from $C_1$-$C_3$ Oxygenate Compounds According to the present invention an improved hydrogenation process is provided for the preparation of a $C_1$-$C_3$ hydroxy compound, comprising the steps of:
  a) Providing an oxygenate feed composition comprising a $C_1$-$C_3$ oxygenate compound, and
  b) Providing a hydrogenation catalyst material comprising Cu on carbon, then
  c) Reacting the composition of step a) with hydrogen in the presence of the catalyst of step b) and under conditions to provide gas phase hydrogenation of the oxygenate compound to obtain a hydrogenation product composition, and then
  d) Recovering the hydrogenation product composition.

The hydrogenation process according to the present invention has the advantages of being more efficient than known processes; enabling the use of the oxygenate containing product of thermolytic fragmentation of sugar compositions as feed for the preparation of the corresponding hydroxy compounds at high selectivity and high yield; eliminating the need for non-aqueous solvents in the hydrogenation process; enabling the use of cheaper catalysts; reducing byproduct production; enabling purification on an industrial scale; and being unaffected by the presence of additional compounds such as formaldehyde. In fact, in the process according to the present invention, formaldehyde may decompose into $H_2$ and CO in the presence of the Cu/C catalyst. Since $H_2$ is a reactant in the hydrogenation reaction it may be consumed in the hydrogenation reaction in the reactor. The ability to separate byproducts from the ethylene glycol product enables the ethylene glycol to be used in processes such as polymer production. Polymer production requires substrates to be in a highly pure form. All of these desirable advantages makes the production of in particular ethylene glycol from biomaterials such as sugar more attractive industrially and enable processes to become commercially feasible.

In particular, the process according to the invention, which includes using the copper on carbon catalyst in a gas phase hydrogenation, shows significantly improved selectivity and activity compared to conventional gas phase aldehyde hydrogenation catalysts, such as Cu/ZnO/$Al_2O_3$ (U.S. Pat. Nos. 4,762,817, 5,155,086 and 5,302,569). In fact, almost quantitative yields of ethylene glycol may be obtained. Furthermore, the productivity of ethylene glycol and propylene glycol is approx. 30% higher than the conventional gas phase catalyst; a very surprising discovery considering the copper loading is 10 times higher for the conventional catalyst. Thus the activity on a metal basis is 13 times higher for the active carbon based catalyst. As the metal costs constitute a significant portion of the total catalyst cost, such a dramatic reduction in the required amount of metal translates into a significantly cheaper catalyst. Also, the copper on carbon catalytic material is quite unaffected by formaldehyde present in the feed.

In an embodiment of the present invention, the $C_1$-$C_3$ oxygenate compound of the oxygenate feed composition of step a) is a $C_2$-$C_3$ oxygenate compound. In another embodiment of the present invention, the oxygenate feed composition of step a) comprises one or more $C_1$-$C_3$ oxygenate compounds selected from the group consisting of glycolaldehyde, glyoxal, pyruvaldehyde, acetol and formaldehyde. In yet another embodiment of the present invention, the oxygenate feed composition comprises at least two of the $C_1$-$C_3$ oxygenate compounds selected from the group consisting of glycolaldehyde, glyoxal, pyruvaldehyde, acetol and formaldehyde. When the oxygenate feed composition is a fragmentation product of a thermolytic fragmentation of a sugar composition, it will contain all of the above $C_1$-$C_3$ oxygenate compounds in various amounts. The amount of each compound will depend on the fragmentation conditions, but in general, it will be within the following ranges by weight per total weight of oxygenates: glycolaldehyde 40-85%, glyoxal 2-5%, pyruvaldehyde 7-30%, acetol 1-10% and formaldehyde 1-25%.

In an embodiment of the present invention, the hydrogenation product composition of step d) comprises one or more $C_1$-$C_3$ hydroxy compounds selected from the group consisting of methanol, ethylene glycol and propylene glycol. In another embodiment according to the present invention, the $C_1$-$C_3$ hydroxy compound of the hydroxy product composition of step e) is a $C_2$-$C_3$ hydroxy compound.

The process according to the present invention may be performed under continuous conditions. This is an advantage, on industrial scale, since continuous processes are more efficient. In general, the process may be conducted in a chemical reactor comprising i) an inlet zone in fluid communication with ii) a reaction zone comprising a heterogeneous hydrogenation catalyst material in fluid communication with iii) an outlet zone. The process may be conducted in a Berty reactor, a packed bed reactor, a fixed bed reactor, a multi-tubular reactor or a fluid bed reactor.

As the hydrogenation reaction is highly exothermic, it is desirable to choose reactors having means to control the temperature rise in the reactor. Some reactors suitable for heat removal could be, but is not limited to, multi-tubular reactors, reactors having cooling between the different catalyst layers (inter-bed cooling) or recycle reactors.

One feasible reactor concept is a sub-category of the fixed/packed bed, where the catalyst is divided between numerous tubes and these tubes are positioned in a heat transfer media. The heat transfer media could be boiling water which upon evaporation absorbs heat from the exothermic reaction and thus produces steam to be used elsewhere in the process. This reactor concept is known as a multi-tubular fixed bed reactor or a boiling water reactor.

Another feasible reactor concept is a fluidized bed with immersed cooling coils. This reactor can provide a very good temperature control and also produce steam. Comparing the chemical reaction performance of the multi-tubular fixed bed reactor and fluidized bed reactor, the first will provide a higher degree of plug flow behavior for the gas phase and the second reactor a higher degree of isothermal conditions.

Under continuous conditions, the reactor fluid will in general be led from the outlet zone through an outlet. This fluid is also referred to as the hydrogenation product composition and comprises the $C_1$-$C_3$ hydroxy compound. The hydrogenation product composition may be led directly to a purification unit or may be collected.

In an aspect of the invention, the oxygenate feed composition of step a) is brought into the gas phase prior to step c) of hydrogenating the oxygenates, e.g. using a spray nozzle. In an embodiment, the oxygenate feed composition of step a) is provided as a gas phase composition. This has the advantage that a gaseous oxygenate feed composition may be fed to the hydrogenation reactor without a prior step of evaporating it. Nor is condensation of the fragmentation product composition needed.

In an aspect of the present invention, the hydrogenation catalyst material of step b) has a loading of Cu on carbon in the range of from 0.1 to 70 weight percent, such as from 1 to 20 or from 2 to 15 or from 4 to 10.

In an aspect of the present invention, step c) is conducted under an initial hydrogen partial pressure of at least 0.5 bar, such as at least 0.6 or 0.7 or 0.8 or 0.9 or 1.0 bar or in the range of from 0.5-10 bar or 0.7-5 bar. According to an embodiment of the present invention, the initial oxygenate molar fraction in step c) is from 0.001 to 0.5, such as from 0.01-0.5, 0.05 to 0.3 or from 0.1 to 0.2. The hydrogen gas may be fed to the reactor in the form of a pure hydrogen gas or in the form of a hydrogen gas comprising impurities such as carbon monoxide. Carbon monoxide will not interfere with the hydrogenation reactions. In the presence of water, it will be converted into carbon dioxide and hydrogen over the catalytic material.

Step c) of the process according to the present invention may be conducted under a total pressure of from 0.8-500 bar, such as from 0.9-100 or 0.9-10 bar. The reaction temperature of step c) may be in the range of from 100-400° C., such as from 150-300° C., 200-250° C.

According to an embodiment of the present invention, step c) of reacting the oxygenate feed composition with hydrogen in the presence of the hydrogenation catalyst material is conducted in a chemical reactor. Chemical reactors suitable for continuous operation of the process according to the present invention, preferably have one or more inlets and one or more outlets, e.g. one or more of an oxygenate feed inlet, a hydrogen inlet, a catalyst inlet, and one or more of a hydrogenation product outlet, a spent catalyst outlet, an excess gas outlet.

According to another embodiment of the present invention, the process is conducted with a ratio of flow rate by weight of oxygenate feed composition of step a) to weight of catalytic material of step b) loaded to the reactor in the range of from 0.001 to 1000 g $C_1$-$C_3$ oxygenate compounds per g catalyst per hour, such as from 0.01 to 500 or from 0.1 to 400 g $C_1$-$C_3$ oxygenate compounds per g catalyst per hour.

According to an embodiment of the present invention, the hydrogenation product composition obtainable by the process according to the present invention, may comprise one or more of the $C_1$-$C_3$ hydroxy compounds selected from methanol, ethylene glycol and propylene glycol. When the oxygenate feed composition is a fragmentation product of a thermolytic fragmentation of a sugar composition, the various $C_1$-$C_3$ oxygenate compounds will be converted into the corresponding hydroxy compounds. The hydrogenation product composition will accordingly contain all of the above $C_1$-$C_3$ hydroxy compounds in various amounts. The amount of each compound will depend on the fragmentation conditions. According to an embodiment of the present invention the hydrogenation product composition comprises methanol in the range of from 0-25%, ethylene glycol in the range of from 35-90% and propylene glycol in the range of from 5-40% by weight per total weight of hydroxy compounds.

Preferred $C_1$-$C_3$ hydroxy compounds are ethylene glycol and propylene glycol. An advantage of the process according to the invention is that the selectivity towards ethylene glycol is at least 80% (moles of ethylene glycol formed per mole $C_2$-oxygenate (glycolaldehyde, glyoxal) converted), preferably at least 85, 88, 90, 91, 92, 93, 94, 95, 96 or 97%, and the selectivity towards propylene glycol is at least 60% (moles of propylene glycol formed per mole $C_3$-oxygenate (pyruvaldehyde, acetol) converted), preferably at least 85, 88, 90, 91, 92, 93, 94, 95, 96 or 97%.

In addition, the hydrogenation product composition obtainable by the process according to the present invention, may contain solvent added in the thermolytic fragmentation process.

The hydrogenation product composition of d) may be subjected to a purification step, such as distillation, filtration, adsorption and/or ion exchange.

Process of Producing $C_1$-$C_3$ Hydroxy Compounds from Sugar Compositions

According to the present invention, a process for the preparation of a $C_1$-$C_3$ hydroxy compound from a sugar composition is provided, comprising the steps of:
  i. Providing a feedstock solution of a sugar composition;
  ii. Exposing the feedstock of a) to thermolytic fragmentation to produce a fragmentation product composition comprising a $C_1$-$C_3$ oxygenate compound; and
  iii. Optionally conditioning the fragmentation product composition; and then
  iv. Subjecting the fragmentation product composition of step ii) or iii) to the hydrogenation process according to the present invention, wherein the fragmentation product composition becomes the oxygenate feed composition of step a) of the hydrogenation process according to the present invention.

Since the fragmentation product composition is already in the gaseous phase, an advantage of conducting a gas phase hydrogenation of the product obtainable from thermolytic fragmentation of a sugar composition is that a step of evaporating the oxygenate feed composition can be avoided. Instead the gaseous thermolytic fragmentation product may be led directly to a hydrogenation unit for hydrogenation of the $C_1$-$C_3$ oxygenate compounds into $C_1$-$C_3$ hydroxy compounds.

"Directly" is intended to refer to a transfer from the fragmentation unit to the hydrogenation unit which is not interrupted by significant delays nor by condensation. Preferably the outlet of the fragmentation unit is directly, fluidly connected with the inlet of the hydrogenation unit by means of piping equipment suitable for conveying high temperature gases.

The optional conditioning of step iii) may comprise a distillation, filtration, adsorption and/or ion exchange to remove impurities prior to the hydrogenation.

The sugar composition of the feedstock solution for thermolytic fragmentation may be selected from one or more of the monosaccharides fructose, xylose, glucose, mannose, galactose, arabinose; the disaccharides sucrose, lactose, maltose or from syrups such as corn syrup, cane sugar syrup or whey. The feedstock solution of step i) is generally a solution of a sugar in a solvent comprising from 20-95, such as from 50-90 wt % of sugar. The solvent may comprise one or more of the compounds selected from the group consisting of water, methanol, ethanol, ethylene glycol and propylene glycol. It is an advantage in the fragmentation step to use solvents comprising alcohols, since the evaporation energy is lower than water.

$C_1$-$C_3$ hydroxy products such as ethylene glycol and propylene glycol obtained from bio materials such as sugars, will have a significantly higher content of $^{14}C$ carbon than the same products obtained from petrochemical sources.

Accordingly, a product is provided according to the present invention, which is obtainable by the process for the preparation of a $C_1$-$C_3$ hydroxy compound from a sugar composition described above. Such a product is characteristic by having a $^{14}C$ content above 0.5 parts per trillion of the total carbon content. The $C_1$-$C_3$ hydroxy compound may be ethylene glycol and at least 70% of the initial carbon may be recovered in the form of ethylene glycol or propylene glycol. According to an embodiment of the present invention, a product is provided which is obtainable by the process according to the present invention, which is characterized in that the product has a $^{14}C$ content above 0.5 parts per trillion (weight by weight) of the total carbon content; and in that at least 70% of the initial carbon is recovered in the form of ethylene glycol or propylene glycol in the hydrogenation product composition.

The $C_1$-$C_3$ hydroxy compound prepared according to the invention, such as ethylene glycol or propylene glycol, may be used for the preparation of a polymer, such as polyethylene terephthalate, polyester resins, fibres or films. The polymer will have a $^{14}C$ content reflecting the fraction of monomers which have been obtained from biomaterials.

The $C_1$-$C_3$ hydroxy compound prepared according to the invention, such as ethylene glycol or propylene glycol, may also be used as a de-icing agent, coolant, anti-freeze agent or solvent.

In and embodiment according to the present invention a system for continuously performing the process disclosed herein is provided, said system comprising a hydrogenation unit, such as a multi-tubular reactor, having an inlet and an outlet and a catalyst according to the present invention, and a thermolytic fragmentation unit having an inlet and outlet, wherein the outlet of said thermolytic fragmentation unit is fluidly connected to the inlet of said hydrogenation unit. In an embodiment according to the present invention, the outlet of said thermolytic fragmentation unit is directly, fluidly connected to the inlet of said hydrogenation unit. The fragmentation unit comprises a fragmentation reactor comprising suitable inlets for feedstock and heat carrier particles and outlets for a fragmentation product composition (stream) and spent heat carrier particles. The hydrogenation unit comprises a chemical reactor comprising suitable inlets for the oxygenate feed composition and hydrogen and outlets for a hydrogenation product composition (stream) and excess hydrogen.

In an embodiment according to the present invention, the outlet of the fragmentation unit is directly, fluidly connected with the inlet of the hydrogenation unit by means of piping equipment suitable for conveying high temperature gases. "Directly" is intended to refer to a transfer from the fragmentation unit to the hydrogenation unit which is not interrupted by significant delays nor by condensation/evaporation or purification. An advantage of direct transfer of fragmentation product to hydrogenation unit is that the heat remaining in the fragmentation product may be retained and as the hydrogenation is a gas phase hydrogenation a step of evaporating the feed may be dispensed with, since it is already in the gas phase.

In another embodiment according to the present invention, the system further has a hydrogen recycle from the outlet of the hydrogenation unit to the inlet or the hydrogen inlet of the hydrogenation unit. Accordingly, excess hydrogen may be recycled to the hydrogenation unit thus improving cost efficiency. The recycle may be connected with the hydrogen inlet or may be recycled directly into the chemical reactor.

BRIEF DESCRIPTION OF THE DRAWINGS

FIG. 2: Selectivity towards ethylene glycol and productivity obtained in the hydrogenation of a $C_1$-$C_3$ oxygenate feed composition over a commercial Cu/ZnO/Al$_2$O$_3$ catalyst at 220° C.

DEFINITIONS

Figure 1:
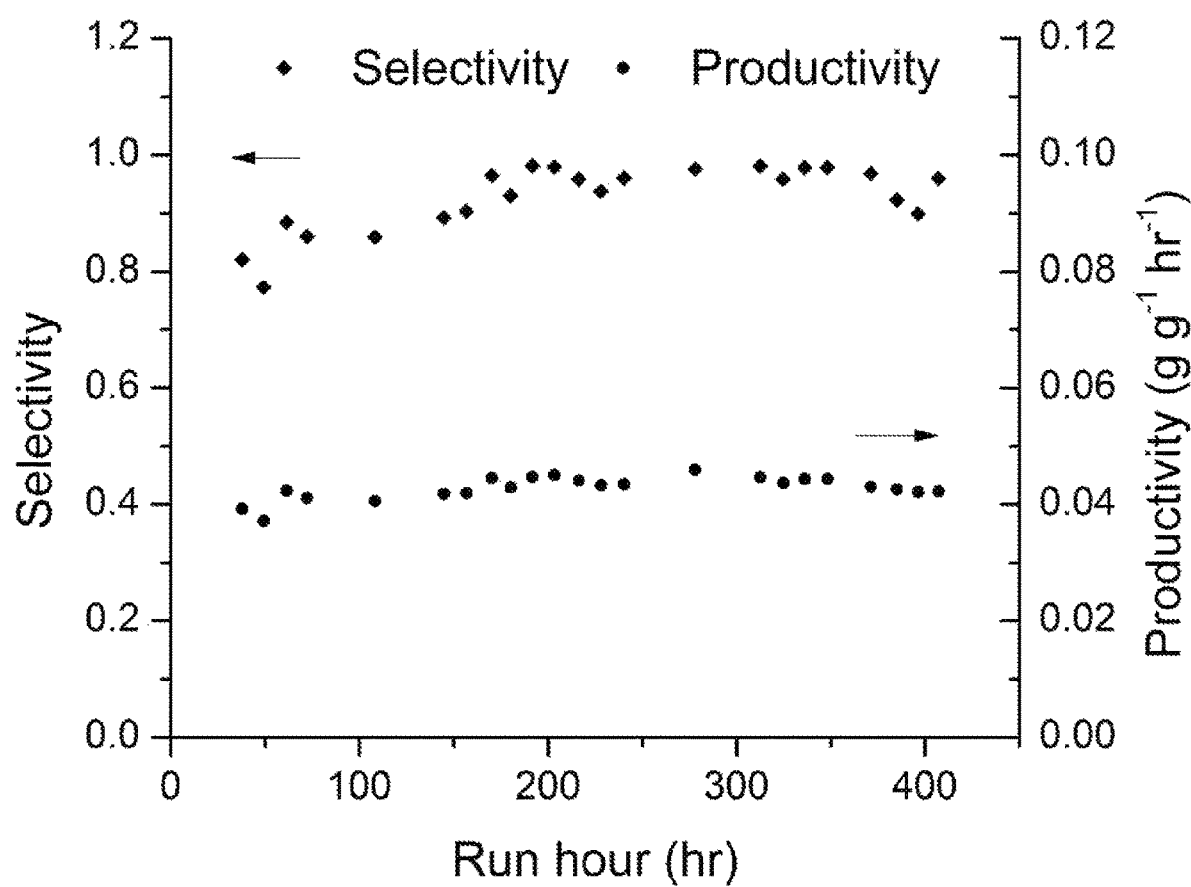
FIG. 1: Selectivity towards ethylene glycol and productivity obtained in the hydrogenation of a $C_1$-$C_3$ oxygenate feed composition over a Cu/C catalyst at 220° C.

The term "oxygenate feed composition" is meant to refer to the oxygenate containing fluid passing through the inlet of the reactor used for conducting the hydrogenation. When the oxygenate feed composition is obtained from a thermolytic fragmentation of a sugar composition, it may in addition to the $C_1$-$C_3$ oxygenate compounds, contain other compounds e.g. organic acids such as acetic acid, formic acid, glycolic acid and/or lactic acid; furans such as furfural and/or 5-hydroxymethylfurfural; and solvents such as water.

In the present context, the term "$C_1$-$C_3$ oxygenate compound" is meant to refer to an organic compound containing between 1 and 3 carbon atoms and at least one carbonyl bond (ketone or aldehyde).

The term "oxygenate feed composition comprising a $C_1$-$C_3$ oxygenate compound" is meant to refer to an oxygenate feed composition comprising one or more $C_1$-$C_3$ oxygenate compounds. It may also comprise minor amounts of other organic compounds.

In the present context, a "gas phase hydrogenation" is meant to refer to a hydrogenation wherein the substrate (here the $C_1$-$C_3$ oxygenate compound) is essentially in a gaseous form in the reaction zone of the reactor. For example, at least 80 wt %, such as at least 90, 92, 94 or 96 wt %, is in the gaseous form. Accordingly, this means that 80-100 wt %, such as 90-100, 92-100, 94-100 or 96-100 wt %, is in the gaseous form.

The term "hydrogenation product composition" is meant to refer to the hydroxy compound containing fluid resulting from the hydrogenation reaction. When the hydrogenation product composition is obtained from hydrogenating the fragmentation product of a thermolytic fragmentation of a sugar composition, it may in addition to the $C_1$-$C_3$ hydroxy compounds, contain other compounds e.g. organic acids such as acetic acid, formic acid, glycolic acid and/or lactic acid; furans such as furfural and/or 5-hydroxymethylfurfural; and solvents such as water.

In the present context, the term "$C_1$-$C_3$ hydroxy compound" is meant to refer to an organic compound which contains between 1 and 3 carbon atoms and at least one hydroxyl group (alcohol) and which may be produced by hydrogenation of a $C_1$-$C_3$ oxygenate compound.

The term "hydrogenation product composition comprising a $C_1$-$C_3$ hydroxy compound" is meant to refer a hydrogenation product composition comprising one or more $C_1$-$C_3$ hydroxy compounds.

The term "catalytic material" is to be understood as any material which is catalytically active. This is also the meaning of the term "catalyst". All terms may be used interchangeably.

The terms "Cu on carbon" and "Cu/C" are meant to refer to a catalytically active material having a support of carbon (such as activated carbon/carbon nanotubes/graphene/fullerenes) with copper particles deposited on the support. As the skilled person will know, it is mainly the surface of the Cu particles which provide the catalytic activity. Accordingly, a large Cu particle surface area is desirable.

The term "Recovering" is meant to refer either to collecting the hydrogenation product composition or to directing the hydrogenation product composition to a subsequent step such as to a purification unit.

The term "yield" is in the present context meant to refer to the molar fraction of $C_1$-$C_3$ oxygenate compound which is converted into its corresponding $C_1$-$C_3$ hydroxy compound (i.e. $C_1$ to $C_1$; $C_2$ to $C_2$; and $C_3$ to $C_3$).

The term "conversion" is in the present context meant to refer to the molar fraction of $C_1$-$C_3$ oxygenate compound which has reacted during the hydrogenation process to form either the desired $C_1$-$C_3$ hydroxy compound or other products.

The term "selectivity" is meant to refer to the molar fraction of desired product formed per substrate converted. In the present context the substrate for a $C_1$ hydroxy compound is only considered to be the $C_1$ oxygenate compounds present in the oxygenate feed composition; for a $C_2$ hydroxy compound the substrate is only considered to be the $C_2$ oxygenate compounds present in the oxygenate feed composition; and for a $C_3$ hydroxy compound the substrate is only considered to be the $C_3$ oxygenate compounds present in the oxygenate feed composition. The selectivity may be calculated as yield divided by conversion.

The term "productivity" is meant to refer to the amount by weight of product produced over the catalyst per weight of catalyst per hour. So if ethylene glycol (EG) is the desired product, the productivity is considered the amount by weight of EG produced over the catalyst per weight of catalyst per hour. If propylene glycol (PG) is the desired product, the productivity is considered the amount by weight of PG produced over the catalyst per weight of catalyst per hour. If both EG and PG are the desired products, the productivity is considered the amount by weight of EG and PG produced over the catalyst per weight of catalyst per hour.

The term "initial hydrogen partial pressure" and the term "initial oxygenate molar fraction" are meant to refer to the partial pressure or molar fraction at the time when it first meets the catalytic material.

The term "continuous conditions" is meant to refer to truly continuous conditions (such as in a fluid bed reactor or packed bed reactor, optionally with recycle of the hydrogenation product composition to the feed stream or to the reactor inlet) but it is also meant to refer to semi-continuous conditions such as repeatedly feeding small portions of the oxygenate feed composition to the reactor fluid and repeatedly collecting small portions of the hydroxyl product composition from the reactor outlet.

EXAMPLE

Example 1: Gas Phase Hydrogenation of Oxygenate Feed Composition in the Presence of Cu/C An aqueous fragmentation mixture (fragmentation product composition) containing 80 g/L of glycolaldehyde, 7 g/L of formaldehyde, 5 g/L of pyruvaldehyde, 1 g/L of acetol and 1 g/L of glyoxal was prepared as described in U.S. Pat. No. 7,094,932: A bed of sand was fluidized with nitrogen and heated to 520° C. A 10 wt. % solution of glucose in water was injected into the bed through an atomization nozzle. After passing through the bed, the product was cooled in a condenser and the liquid product collected. The mixture was distilled to remove high boiling impurities and was subjected to the hydrogenation by the process described below without any further pretreatment.

The hydrogenation was performed as follows: 25 g of the catalyst was loaded in a fixed bed reactor (I.D. 22 mm) and reduced in situ at 220° C. for 6 hours in a flow of 5% hydrogen in nitrogen. The temperature was maintained at the same level after reduction. The flow was changed to 100% hydrogen and increased to 6.5 Nl/min. The substrate (fragmentation product composition/oxygenate feed composition) was injected into the reactor, at a rate of 0.25 g/min, from the top through a two fluid nozzle, using the hydrogen stream to atomize the liquid. The pressure at the reactor inlet was at these conditions 1.05 bar, giving a hydrogen partial pressure at the reactor inlet of 1.0 bar.

After passing through the catalyst bed, the product was cooled in a condenser and the liquid product collected (hydrogenation product composition). In FIG. 1 the selectivity towards ethylene glycol is shown for the gas phase hydrogenation of the fragmentation mixture over Cu/C catalyst. As can be seen the selectivity is 90-100% towards ethylene glycol.

Example 2: Gas Phase Hydrogenation of Oxygenate Feed Composition in the Presence of Cu/ZnO/$Al_2O_3$ A commercial Cu/ZnO/$Al_2O_3$ gas phase hydrogenation catalyst was used for hydrogenating the oxygenates (aldehydes) of the fragmentation mixture according to the same procedure as described above. The yields are not as good. In FIG. 2 the selectivity towards ethylene glycol is shown for the gas phase hydrogenation of the fragmentation mixture over a commercial Cu/ZnO/$Al_2O_3$ catalyst. As can be seen the selectivity is only 75-80% towards ethylene glycol.

The hydrogenation of an $C_1$-$C_3$ oxygenate feed composition over catalysts based on copper supported on active carbon gives significantly improved yields. In fact, nearly quantitative yields of ethylene glycol are obtainable as shown here. The productivity of ethylene glycol (EG) of the active carbon based catalyst is approx. 30% higher than the conventional catalyst; a very surprising discovery considering the copper loading is 10 times higher for the conventional catalyst. Thus the activity on a metal basis is 13 times higher for the active carbon based catalyst. As the metal costs constitute a significant portion of the total catalyst cost, such a dramatic reduction in the required amount of metal translates into a significantly cheaper catalyst.

Example 3: Direct Gas Phase Hydrogenation of the Gaseous Fragmentation Product Composition During the fragmentation process, a high-boiling, black, and highly viscous byproduct is formed, which must be removed from the fragmentation product composition. The byproduct is a complex mixture of various oxygenates and saccharides, which has partly oligomerized forming a tar-like substance. This tar-like product is considered an unwanted byproduct and an object of the current invention is to minimize the formation of this.

The tar-like substance can be removed by vacuum distillation. Heating an oxygenate feed composition or a hydrogenation product composition to 150° C. at 20 mbar in a rotary evaporator allows for the collection of the desired $C_1$-$C_3$ oxygenate compounds or $C_1$-$C_3$ hydroxy compounds as the distillate, while the tar-like substance is collected as the residue.

Removing the tar-like substance by vacuum distillation from a fragmentation product composition/oxygenate feed composition produced by a method similar to the first step of example 1 yields approx. 5 wt. % of the total dry matter content of the oxygenate feed composition as a tar-like substance.

The $C_1$-$C_3$ oxygenate feed composition produced in a manner similar to the first step of example 1 may be hydrogenated in the liquid phase over a Ru/C catalyst as described in WO 2016/001169 A1. The tar-like substance may then be removed by vacuum distillation of the hydrogenation product composition, which yields approx. 19 wt. % of the total drymatter content of the hydrogenation product composition as a tar-like substance.

The oxygenate feed composition produced in a manner similar to the first step in example 1 may alternatively be hydrogenated in the gas phase by the procedure described in part 2 of example 1 without an intermediate step of condensing and subsequently evaporating the oxygenate feed composition. This can be performed by directing the $C_1$-$C_3$ oxygenate compound containing gas stream leaving the fragmentation reactor directly to the hydrogenation reactor. A hydrogenation product composition is collected by condensing the products leaving the hydrogenation reactor. The tar-like substance may then be removed by vacuum distillation of the hydrogenation product composition, which yields approx. 3 wt. % of the total dry matter content of the hydrogenation product composition as a tar-like substance.

As can be seen, performing the hydrogenation directly after the fragmentation reaction, without an intermediate step of condensing and optionally evaporating the oxygenate feed composition prior to conducting a gas phase hydrogenation leads to a significant reduction of the amount of produced tar-like substance.

The invention claimed is:

1. A process for the preparation of ethylene glycol, comprising the steps of:
   a) providing an oxygenate feed composition comprising a $C_1$-$C_3$ oxygenate compound, wherein the composition comprising $C_{1-3}$-oxygenate compounds comprises glycolaldehyde and at least one of glyoxal and carboxylic acid, and
   b) providing a hydrogenation catalyst material comprising Cu on carbon, then
   c) reacting the composition of step a) with hydrogen in the presence of the catalyst of step b) and under conditions to provide gas phase hydrogenation of the oxygenate compound to obtain a hydrogenation product composition comprising ethylene glycol, and then
   d) recovering the hydrogenation product composition.

2. The process according to claim 1, wherein the process is performed under continuous conditions.

3. The process according to claim 1, wherein the oxygenate feed composition of step a) is brought into the gas phase by atomizing the oxygenate feed using an atomization nozzle.

4. The process according to claim 1, wherein the oxygenate feed composition comprises glycolaldehyde, glyoxal and at least one of the $C_1$-$C_3$ oxygenate compounds selected from the group consisting of pyruvaldehyde, acetol and formaldehyde.

5. The process according to claim 1, wherein the oxygenate feed composition of step a) is brought into the gas phase prior to step c).

6. The process according to claim 1, wherein the hydrogenation catalyst material of step b) has a loading of Cu on carbon in the range of from 0.1 to 70 weight percent.

7. The process according to claim 1, wherein step c) is conducted under an initial hydrogen partial pressure of at least 0.5 bar.

8. The process according to claim 1, wherein the initial oxygenate molar fraction in step c) is from 0.01 to 0.5.

9. The process according to claim 1, wherein step c) is conducted under a total pressure of from 0.8-500 bar.

10. The process according to claim 1, wherein step c) is conducted under a temperature in the range of from 100-400° C.

11. The process according to claim 1, wherein step c) of reacting the oxygenate feed composition with hydrogen in the presence of the hydrogenation catalyst material is conducted in a chemical reactor.

12. The process according to claim 11, wherein the oxygenate feed composition is fed to the chemical reactor at a ratio of flow rate by weight of oxygenate feed composition of step a) to weight of catalytic material of step b) in the range of from 0.001 to 1000 g $C_1$-$C_3$ oxygenate compounds per g catalyst per hour.

13. The process according to claim 1, wherein the hydrogenation product composition of d) is subjected to a purification step.

14. The process according to claim 1, wherein unreacted hydrogen recovered after step d), is recycled to step c).

15. The process according to claim 1, wherein the process is conducted in a Berty reactor, a packed bed reactor, a fixed bed reactor, a multi-tubular reactor or a fluid bed reactor.

16. A process for the preparation of ethylene glycol, comprising the steps of:
   i. providing a feedstock solution of a sugar composition;
   ii. exposing the feedstock of a) to thermolytic fragmentation to produce a fragmentation product composition comprising a $C_1$-$C_3$ oxygenate compound; and
   iii. optionally conditioning the fragmentation product composition; and then
   iv. subjecting the fragmentation product composition of step ii) or iii) to the process according to claim 1, wherein the fragmentation product composition is the oxygenate feed composition of step a).

17. The process according to claim 16, wherein the sugar composition is selected from fructose, xylose, glucose, mannose, galactose, sucrose, and lactose.

18. The process according to claim 16, wherein the feedstock solution of step i) is a solution of a sugar in a solvent comprising from 20-95 wt % of sugar.

19. The process according to claim 16, wherein the solvent comprises one or more of the compounds selected from the group consisting of water, methanol, ethanol, ethylene glycol and propylene glycol.

20. The process according to claim 1, wherein step c) is conducted under a total pressure of from 0.8-10 bar, wherein step c) is conducted under a temperature in the range of from 150-400° C., wherein the hydrogenation product composition of step d) comprises ethylene glycol.

21. The process according to claim 1, wherein the oxygenate feed composition comprises glycolaldehyde and glyoxal.

22. The process according to claim 1, wherein the oxygenate feed composition comprises glycolaldehyde and a carboxylic acid.

23. The process according to claim 1, wherein the oxygenate feed composition comprises glycolaldehyde and a carboxylic acid selected from the group consisting of acetic acid, formic acid, lactic acid and glycolic acid.

* * * * *